United States Patent [19]
Dorsch

[11] 3,937,577
[45] Feb. 10, 1976

[54] ZEEMAN EFFECT ATOMIC ABSORPTION SPECTROMETER

[75] Inventor: Robert R. Dorsch, Wilmington, Del.

[73] Assignee: E. I. Du Pont de Nemours and Company, Wilmington, Del.

[22] Filed: May 15, 1974

[21] Appl. No.: 470,189

[52] U.S. Cl. .................................. 356/85; 356/96
[51] Int. Cl.² ....................... G01J 3/30; G01J 3/42
[58] Field of Search ............................ 356/85–88, 356/96, 97

[56] References Cited
UNITED STATES PATENTS

| | | | |
|---|---|---|---|
| 3,586,441 | 6/1971 | Smith et al. | 356/87 X |
| 3,600,567 | 8/1971 | Varnela | 235/196 |
| 3,676,004 | 7/1972 | Prugger et al. | 356/87 |
| 3,737,234 | 6/1973 | Shibata | 356/88 |
| 3,740,117 | 6/1973 | Hubby, Jr. | 350/149 |
| 3,752,995 | 8/1973 | Liedholz | 250/214 R |
| 3,811,778 | 5/1974 | Hadeishi | 356/85 |
| 3,843,258 | 10/1974 | Shupe | 356/88 |

OTHER PUBLICATIONS

Hadeishi et al., "Hyperfine Zeeman Effect Atomic Absorption Spectrometer for Mercury," Science, Vol. 174, Oct. 22, 1971, pp. 404–407.

Primary Examiner—Alfred E. Smith
Assistant Examiner—F. L. Evans

[57] ABSTRACT

An acyclic Zeeman effect atomic absorption spectrometer viewing the sample analyzed continuously and simultaneously with two linear orthogonally polarized radiation beams preselected as to wavelength to effectively cancel out, upon logarithmic ratioing of their electrical analogs, the contribution of adulterants to the mass determination of a trace element in analysis and thereafter obtaining the ratio of the integrated value of the monitored sample logarithmic ratio signal with that of a stored standard sample integrated logarithmic ratio signal as a measure of the concentration of trace element present.

8 Claims, 12 Drawing Figures

ZEEMAN EFFECT ATOMIC ABSORPTION SPECTROMETER

BRIEF SUMMARY OF THE INVENTION

Generally, this invention relates to an acyclic Zeeman effect spectrometer particularly suited to industrial in-plant trace metal monitoring utilizing a transverse D-C magnetic field to continuously resolve the radiation from an unmodulated sharp spectral line source into linear orthogonally polarized components, a preselected one of which, the analytical beam, has a specific frequency characteristic of the element to be analyzed, whereas a preselected other of which, the reference beam, has frequencies different from the analytical beam, sample atomizing furnace means open to the passage of both beams, optical means segregating the analytical and reference beams along separate courses each provided with electronic transducing means generating an electrical signal corresponding to the radiation intensity of the respective beam viewed, means deriving the logarithmic ratio of the electrical signals one to another, and means utilizing the integrated logarithmic ratio to give the concentration of the element in analysis in the sample.

BACKGROUND

Trace metal monitoring has become increasingly important recently in connection with efforts to avoid environmental pollution, and there now exists legislation prescribing extremely low maximum tolerable concentrations of, for example, less than one part per million (p.p.m.) for certain metals such as Hg, Pb, Cd and As in waste streams.

The Environmental Protection Agency has recognized atomic absorption analysis as a preferred technique for most trace metals because of its inherent excellent sensitivity and selectivity capabilities when compared with titration, colorimetry and ion selective electrode techniques. However, conventional atomic absorption techniques do not provide the resolution required to distinguish the presence of trace metals from those matrices which produce strong background absorption signals.

Other shortcomings in conventional atomic absorption spectrometry include a failure to recognize fully the significance of lamp drift and furnace-generated noise in their effects on measurement accuracy. Specifically, means such as flame atomizers have been resorted to with various beam chopping devices to limit the introduction of noise into the measurement signal. However, when an analysis is completed within a short time span, e.g., of the order of two seconds, chopping rates must necessarily be very high in order to avoid the noise problem.

Moreover, standard dual beam atomic absorption analytical techniques do not direct the reference beam through the sample, but, instead, pass the reference beam around it. This precludes correction for background absorption in the measurement signal. In those conventional systems which use a second light source for background absorption correction by passing radiation through the sample, lamp drift correction is precluded. In addition, those spectrometers employing two lamps, two detectors and two synchronized choppers will experience the effects of photomultiplier (PM) tube drift unless the analysis is performed in a short time span. Finally, previous Zeeman effect systems have relied upon complex or fragile devices such as mechanical or electro-optical beam choppers or expensive single purpose filters, such as the atomic vapor filter described by Hadieshi and McLaughlin (ref: Science Oct. 22, 1971) to separate the two beams.

Successful application of atomic absorption analysis to industrial service requires simplicity of control (or, preferably, automation) to permit use by relatively unskilled personnel, system ruggedness to withstand long term service in demanding environments, measurement repeatability in order to detect immediately the onset of effluent system malfunctions, flexibility in the accommodation of product line changes and low maintenance requirements. It is the object of this invention to provide an improved Zeeman effect atomic absorption spectrometer which solves all of the foregoing problems.

The Zeeman effect is the phenomenon that, when an emitting atomic mass in the atomized (i.e., atomic vapor) state is placed in a magnetic field, the emitted radiation, in a direction normal to the magnetic field, propagates as two distinctive linearly but orthogonally polarized beams of equal intensity. One beam, hereinafter denoted the "analytical beam," polarized parallel with the magnetic field, contains a wavelength, $\lambda_\pi$, which is nearly identical with the wavelength of the emitting source in the absence of the magnetic field. The other beam, hereinafter denoted the "reference beam", is polarized orthogonally with respect to the analytical beam and consists of radiation of at least two different wavelengths, $\lambda_{\sigma+}$ and $\lambda_{\sigma-}$, which lie equally spaced on either side of the central $\lambda_\pi$ radiation. The separation in wavelength between the reference and analytical beams is very small, being only on the order of a hundredth of an angstrom unit ($10^{-8}$ cm.), dependent on the strength of the magnetic field. Thus, if one chooses a wavelength of the analytical beam to coincide with the characteristic spectral absorption line of a trace element in the atomized state which it is desired to analyze, the other (reference) beam can effectively monitor the substantially wavelength-independent background absorption characteristic of the analyte.

In order to reduce noise which interferes with the conduct of analysis, this invention resorts to acyclic beam generation and processing, in that it utilizes substantially steady state D-C magnetic field application to the radiation emitter and thereafter employs continuous form analytical and reference radiation beams. The beams are separated spatially by a polarizing prism which is provided with a monochromator or a selected narrow band pass optical thin film filter to block off extraneous background radiation, after which the intensities are separately transduced to electrical analog signals and the logarithmic ratio taken to nullify the effects of strong background absorption and source intensity drift on the trace element mass measurement.

Optional features improving operation constitute a long lifetime resistively heated metallic tubular furnace, a digital reference signal storage means to reduce the need for repeated calibrations, automatic sequencing of programmable analysis steps, and collocation of the monochromator and the polarizing prism to simplify instrument alignment.

Measurement repeatability is enhanced by the use of non-reactive tubing in the sampling system together with complete purging of the microsampler itself to safeguard against sample contamination. A base line clamping circuit is used to nullify slow drifts in the P.M. tubes and preceding circuitry, whereas the ratioing of the dual beams compensates for spectral line source base line drift.

DRAWINGS

The following drawings constitute part of this specification, in which:

FIG. 1A is a perspective view detailing the sample injection sub-assembly of FIG. 1, FIGS. 2A-2E, inclusive, are diagrammatic representations of the several spectra and electrical waveforms existing at the points in FIG. 1 denoted by the respective letter postscripts of these FIGS., wherein FIG. 2AA is a typical spectral line emitted by a narrow spectral line radiation source, in this instance for the element Pb, without magnetic field, FIG. 2A' is a typical spectrum of the radiation beam of FIG. 2A showing the result of Zeeman splitting effected by a transverse D-C magnetic field, FIG. 3 is a schematic diagram of representative reference and analytical signal magnitudes measured for a typical industrial waste effluent, together with the Pb trace metal read-out resulting from the obtainment of the logarithmic ratio of these signals.

DETAILED DESCRIPTION

The Zeeman effect is obtained by relatively moderate strength transverse magnetic fields and, while the "splitting" generally produces a multiplicity of components, this invention treats this multiplicity of components as three significant groups. These groups are plane-polarized with the central group (i.e., $\pi$ components) polarized with its electric vector parallel with the magnetic field lines, whereas the bracketing groups (i.e., the $\sigma+$ and $\sigma-$ groups) are polarized with their electric vectors orthogonal to the magnetic field lines (refer to vector sketch of FIG. 1, location A). Hereinafter, for simplicity in the description, these three groups will be treated as three distinct spectral lines.

The $\pi$ line remains essentially unchanged in wavelength over the original excited wavelength, but the $\sigma+$ and $\sigma-$ lines propagate at higher and lower wave numbers, respectively. In this invention, the $\pi$ line constitutes the "analytical beam," because its wavelength matches the absorption line characteristic of the trace element in analysis, whereas the combined $\sigma$ lines are used collectively as the "reference beam."

An important advantage resides in employing the Zeeman effect in spectral analysis, because the Zeeman effect "splittings" are functions only of the magnetic field and the angular momentum quantum numbers of the atomic state, and not of the energy levels of the atom. Accordingly, it is practicable to select from the several possible absorption lines for a given element the particular line which yields the best Zeeman "splitting" pattern. This choice is facilitated by the results of a calculation of the shift in electron energy $\Delta E = \mu_B |M_J H| g_J$ where $\mu_B$ is the value of the Bohr magneton
$M_J$ is the magnetic quantum number
H is the magnetic field strength, and
$g_J$ is the Lands g factor.

An element-by-element computation of the best Zeeman "splitting" patterns has shown that the mass concentrations of most elements in the periodic table which are susceptible to conventional atomic absorption analysis can be determined by Zeeman effect atomic absorption analysis.

Figure 1:
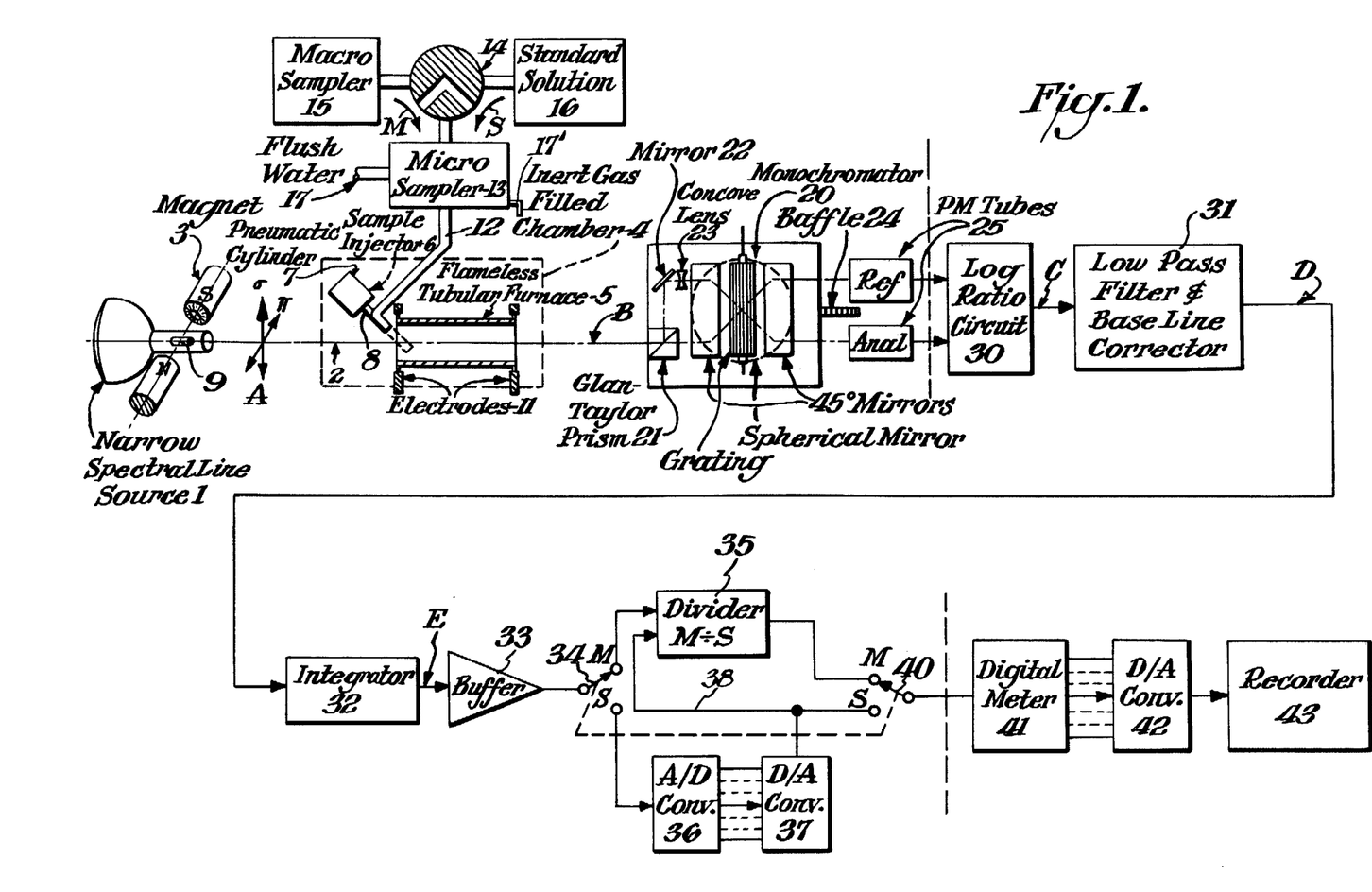
FIG. 1 is a schematic diagram of a preferred embodiment of an analyzer according to this invention showing, also, associated sampling and electronic auxiliaries which, while not essential to operation, are desirable adjuncts to an automated system.

Referring to FIG. 1, a preferred embodiment of apparatus according to this invention, inclusive of the optional features hereinbefore mentioned generally, comprises the three sections set off one from the other by broken vertical lines, consisting, in order to radiation and electrical signal progression, of: (a) the spectrometer, (b) signal processing and measurement and (c) data display.

Figure 2A:
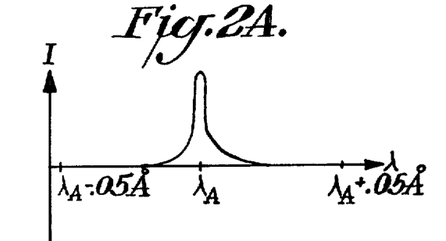

In this instance, the spectrometer utilizes a narrow spectral line source 1, e.g., a hollow cathode lamp the cathode element 9 of which contains the metal which is the subject of analysis. Such lamps are available commercially and may have cathodes composed of five or six metals in association, so that a single lamp can be used at any one time for the analysis of each metal of the group. The radiation emitted from the lamp is projected as a beam 2 having a sharp, highly intense, resonance spectral line against a very low background, wherein the wavelength is identical to that characterizing the trace element in analysis (refer FIG. 2A), $\lambda_A$ for Pb being 2833A with a line width of 0.003A.

For Zeeman "splitting," cathode element 9 must be disposed between the poles of the magnet, and this invention utilizes a D-C magnet 3 which furnishes a noisefree constant D-C field, typically in the range of 2–15K gauss.

The analytical ($\pi$) and reference ($\sigma^+$, $\sigma^-$) beams pass simultaneously and continuously through inert gas-filled chamber 4 via aligned windows, not further detailed herein.

Chamber 4 houses the flameless sample atomizing tubular furnace 5 and the sample injector, denoted generally at 6. Chamber 4 is maintained under a slight positive pressure with a continuously circulated stream of an inert gas (typically argon) which is temporarily increased in pressure just prior to each furnace heating cycle to purge the vapors from the last analysis run. The inert gas must not react with incandescent furnace metal at the atomization temperature of 2,000°–3,000°C. and, additionally, must not cause undue pressure broadening of the absorption spectrum or attenuation of the analytical and reference radiations during the actual analysis portion of the cycle.

Flameless furnace 5 is designed to eliminate the problem of high sporadic emissions, or absorptions, normally observed when flame devices excite matrices (i.e., accompanying background material) containing high concentrations of inorganic salts. Thus, my furnace is fabricated from tantalum in the form of a right circular cylinder having flanged ends, approximately 2.54 cm long × 5.8 mm. inside diameter with a 0.25 mm. wall thickness. The length-to-diameter ratio of approximately 4.4 and the wall thickness settled upon were chosen as a compromise to achieve conflicting desiderata, including maximizing trace element diffusion time (directly a function of tube length but inversely a function of tube diameter), maximizing beam throughput (inversely a function of tube length but directly a function of tube diameter), increasing the service life (directly a function of tube wall thickness) and increasing the electrical resistance for fast heating (inversely a function of wall thickness).

A defect of prior art furnaces has been premature tube fracture resulting from high mechanical stresses imposed by severe thermal gradients existing around sample injection ports provided in the tube walls. To avoid this problem, sample injector 6 is retractable in design (refer FIG. 1A), thereby permitting introduction of the analyte directly into the open radiation entrance end of cylindrical furnace 5.

Figures 1A, 3:
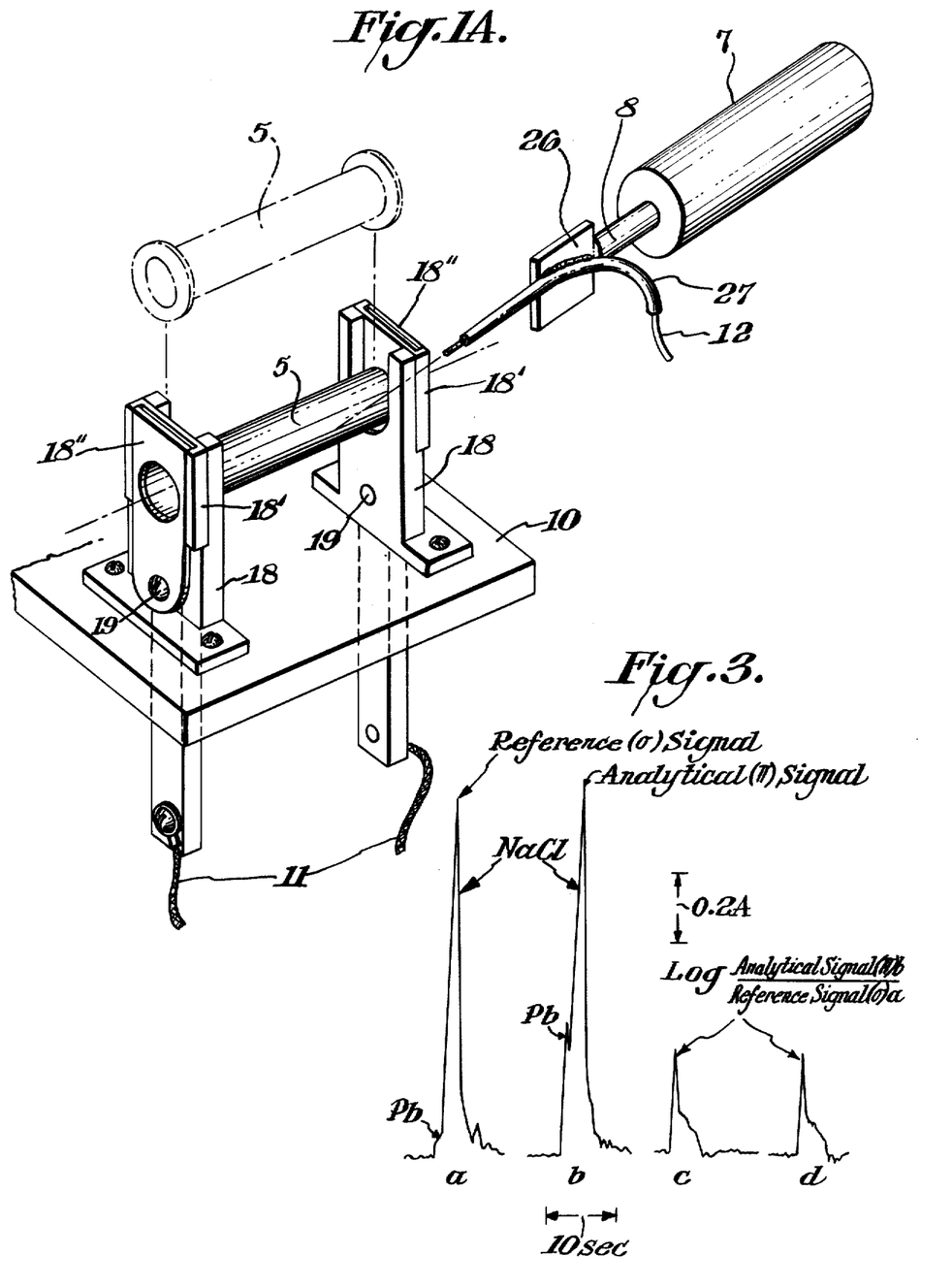

The furnace support comprises a horizontal shelf 10 fabricated from heat-resistant electrical insulator material supported from the side walls of chamber 4, which is provided with upstanding metal posts 18 screw-attached thereto. Posts 18 are cut away at their upper ends to provide open-ended U slots loosely receiving the cylindrical body of furnace 5 with circumferential clearance enough to avoid metal-to-metal heat conduction loss from the furnace body to the support structure. The outboard faces of posts 18 are recessed to receive the lower ends of metal anvil clamp plates 18', which are also provided with open-ended U slots extending from their lower ends in a vertical direction so as to receive furnace 5 loosely therein inboard of the furnace flanges without metal-to-metal contact peripherally of the furnace body per se. The assembly is completed by metal clamp end plates 18" which are drilled centrally to provide circular ports aligning axially with the bore of furnace 5 in set-up position and of the same diameter therewith, which clamps bear on the outside flange faces of the furnace and clamp it firmly against anvil clamp plates 18' when machine screws 19 are tightened. With this design, heat losses from furnace 5 are minimized by restricting metal-to-metal heat conduction paths solely to the end clamp attachments. Electric leads 11 attach to depending extensions of posts 18, furnishing the supply of electrical heating current longitudinally through the wall of furnace 5.

The sampling system, with the exception of the retractable sample injector 6, is conventional equipment incorporating an effluent macro-sampler 15 and a standard solution supply container 16. These are switched at will via two-way valve 14 into connection with the micro-sampler 13, which is provided with flush water supply port 17 and a sample drain port 17' to void surplus analyte continuously supplied to the micro-sampler. Micro-sampler 13, at preselected intervals, meters a small analyte sample of prescribed size (within a 1-100 μ liter range) through non-reactive tubing 12 (e.g., polytetrafluoroethylene) and thence, via sample injector 6, into the radiation entry open end of furnace 5. Micro-sampler 13 then supplies a metered water flush, which cleanses the system to safeguard against trace element carry-over from one analysis cycle to another.

Referring to FIG. 1A particularly, sample injector 6 comprises a pneumatic cylinder 7, piston 8 assembly which carries an outboard metal plate 26 to which is brazed a short length of copper tubing 27. Tubing 27 constitutes a rigid support and guide for flexible polymeric tubing 12 passed therethrough, the outboard end of which is securely retained by friction within tubing 27 with a short length protruding in the direction of furnace 5. The line of advance and retraction of piston 8 and its attached supply tubing is inclined at approximately 15° to the longitudinal axis of furnace 5, thereby permitting withdrawal of the injector sample supply end completely clear of the radiation supply path extending from source 1 through chamber 4 and furnace 5, except during the brief period of sample introduction.

The optical section of the apparatus comprises a polarizing prism 21 and monochromator 20 which are mounted on a common support, not detailed. Since the analytical ($\pi$) and reference ($\sigma$) beams are typically separated in wavelength by only about 0.05A, and hence cannot be spatially separated by a small monochromator, it is first essential to expand their spacing, and this is conveniently done by utilizing their polarization properties.

A polarizing prism 21, such as a Glan-Taylor type, is especially preferred because it separates the two polarizations into two nearly equally intense beams which exit the prism at substantially right angles to one another through adjacent faces. Since the standard Glan-Taylor prism is fabricated from mineral calcite, it becomes opaque to incident radiation at wavelengths shorter than about 2140A. However, the Rochon polarizing prism assembly of FIG. 4, hereinafter described, broadens the analytical capability of this invention through the far ultraviolet range (i.e., to about 1400A) without prohibitive attenuation.

Radiation selectivity is enhanced by employing a monochromator 20, typically a Jarrell Ash grating type with a selectable 2-20A pass band. This apparatus permits one to perform a multi-element analysis simply by setting the monochromator 20 wavelength to that characteristic of the element to be analyzed and adjusting the pass band to essentially exclude spectra lying outside the interval bounded by the $\sigma+$ and $\sigma-$ lines. Collocation of polarizing prism 21 and monochromator 20 permits simultaneous spatial separation of the analytical ($\pi$) and reference ($\sigma$) beams within short spatial limits.

Mirror 22 reflects the horizontally polarized analytical ($\pi$) beam through concave lens 23 and onto the monochromator exit port. The position of lens 23 can be adjusted to neutralize the difference in the two beam path lengths. Opaque radiation baffle 24, attached to the monochromator housing, isolates the analytical and reference beam channels, thereby preventing cross-talk prior to detection by the individual analytical and reference photomultiplier tubes 25, respectively.

Figure 2B:
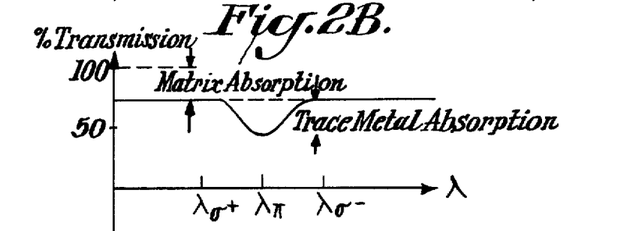
FIG. 2B shows the radiation transmission characteristic of a typical analyte in its atomized state, FIG. 2B' shows the relative intensities of the reference and analytical components of the radiation beam at the sample-atomizing furnace outlet.

Before describing the electronic circuit signal processing, reference is had to FIG. 2B which shows a typical absorption spectrum as obtained from atomized analyte at point B, FIG. 1. In this instance, the reference ($\sigma$) beam experiences a somewhat smaller amount of absorption (practically all due to the matrix materials) than the analytical ($\sigma$) line. However, for high background and small trace element concentrations, the reference ($\sigma$) beam absorption can be almost as large as the analytical ($\pi$) beam absorption. FIG. 2B' shows the absorption build up and decay of reference and analytical beams on the time scale during the brief (approximately 7 sec.) analysis period. An important feature of this invention is that the simultaneous and continuous processing of both the analytical and reference beams practiced ensures that each beam is equally affected by any variations in the spectral line source 1, fogging of chamber 4 inlet and outlet ports, and any furnace-generated matrix noise fluctuations caused by uneven distribution of matrix particulates forming smoke clouds within furnace 5.

Turning now to the electrical signal handling system, the logarithmic ratio of the analytical and reference electrical analog signals generated by the PM tubes 25 transducing the analytical and reference beam intensities is first obtained by conventional log ratio circuit 30. The quantitative relationships upon which trace metal measurement is based are as follows:

According to Beer's law, the intensities of the analytical and reference beams at the outlet of furnace 5 (e.g., at point B) are expressed:

$$I_{Anal.\ Out} = I_{Anal.\ In}\, e^{-\epsilon_1 C_1 l}$$
$$I_{Ref.\ Out} = I_{Ref.\ In}\, e^{-\epsilon_2 C_2 l} \quad \text{where}$$

$I_{Anal.\ Out}$, $I_{Ref.\ Out}$ are the intensities of the analytical ($\pi$) and reference ($\sigma$) beams, respectively, at point B, $I_{Anal.\ In}$, $I_{Ref.\ In}$ are the intensities of the $\pi$ and $\sigma$ beams, respectively, at point A, $l$ = the path length through furnace 5, $\epsilon_1$, $\epsilon_2$ are the mass absorption coefficients at the $\pi$ and $\sigma$ wavelengths, respectively, and $C_1$, $C_2$ are the total mass concentrations within the analyte viewed by the analytical and reference beams, respectively.

Since the Zeeman effect resolves equal intensity radiations:

$$I_\pi = I_{\sigma_-} + I_{\sigma_+},\ \text{and}\ I_{\sigma_-} = I_{\sigma_+}\ \text{then}$$
$$I_{Anal.\ In} = I_{Ref.\ In}$$

It is assumed that $\epsilon_2$ constitutes a valid absorption coefficient at both the $\sigma^+$ and $\sigma^-$ wavelengths, because these wavelengths are very close, usually within 0.1A of each other, and the background absorption is essentially constant over the small range.

Corresponding photoelectric transducer outputs are:
$$J_1 = k_1 I_{Anal.\ Out}$$
$$J_2 = k_2 I_{Ref.\ Out} \quad \text{where}$$

$J_1$, $J_2$ are the photoelectric transducer 25 output currents for the analytical and reference beams, respectively, and $k_1$, $k_2$ are the corresponding PM tube gains.

Taking the logarithm of the ratio of the two output currents yields:

$$\ln\left(\frac{J_1}{J_2}\right) = \ln\left[\frac{k_1 I_{Anal.\ In} e^{-\epsilon_1 C_1 l}}{k_2 I_{Ref.\ In} e^{-\epsilon_2 C_2 l}}\right]$$

but, since $I_{Anal.\ In} = I_{Ref.\ In}$, and $C_1 = C_2$ because both the analytical ($\pi$) and the reference ($\sigma$) beams are spatially coincident as they pass simultaneously and continuously through the atomized sample $$\ln\left(\frac{J_1}{J_2}\right) = \ln\left(\frac{k_1}{k_2}\right) + C_1 l\,(\epsilon_2 - \epsilon_1).$$

The law of additivity prescribes that the absorptivity of the analyte is the sum of the absorptivities of its components parts. Therefore, $$\epsilon_2 C_2 = \epsilon_M (\lambda_\sigma) m_M + \epsilon_B (\lambda_\sigma) m_B$$
$$\epsilon_1 C_1 = \epsilon_M (\lambda_\pi) m_M + \epsilon_B (\lambda_\pi) m_B \quad \text{where}$$

$\epsilon_M (\lambda)$ is the trace element mass absorption coefficient at wavelength $\lambda$, $\epsilon_B (\lambda)$ is the matrix mass absorption coefficient at wavelength $\lambda$, $m_M$ is the trace element mass concentration, $m_B$ is the matrix material mass concentration, and $\lambda$ denotes the wavelength of the viewing beam. But $\epsilon_B (\lambda_\pi) = \epsilon_B (\lambda_\sigma)$ by assumption, therefore $$\ln\left(\frac{J_1}{J_2}\right) = \ln\left(\frac{k_1}{k_2}\right) + l m_M [\epsilon_M (\lambda_\sigma) - \epsilon_M (\lambda_\pi)]$$

which can be simplified and converted to base 10 form by:

$$\log\left(\frac{J_1}{J_2}\right) = C + \alpha m_M \quad \text{where}$$

$$\alpha = lG\,[\epsilon_M(\lambda_r) - \epsilon_M(\lambda_\pi)],\ C = G \ln\left(\frac{k_1}{k_2}\right)$$

and $G = 0.43429$, the logarithm conversion factor, from which it is seen that the output of log ratio circuit 30 provides a direct readout of the amount of trace element in the sample.

The log $J_1/J_2$ is the logarithm of the ratio of transmissivities of the analytical ($\pi$) beam to the reference ($\sigma$) beam. Since the reciprocal relationship constitutes the desired absorptivity ratio, the ratio is inverted by log ratio circuit 30 to give the waveform - log $J_1/J_2$, plotted as the ordinate versus time as the abscissa in FIG. 2C, which is the signal output at point C, FIG. 1. Viewing the plot, it will be seen that the analysis per se commences at time $t_o$, with sample atomization, and is completed approximately 7 secs. later. The maxima of the plot is a direct measure of $\alpha m_M$, i.e., of the trace element mass. The vertical offset indicated is caused primarily by the difference in PM tube gains and log ratio circuit offset.

Figure 2C:
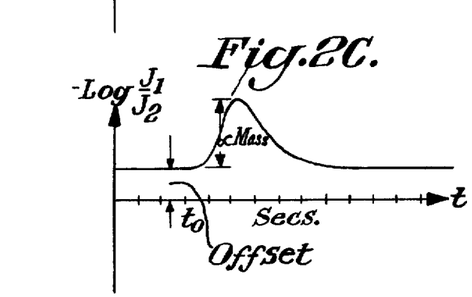
FIG. 2C is a waveform showing the logarithmic ratio of the analytical ($J_1$) to the reference ($J_2$) signals shown in FIG. 2B'.
Figure 2D:
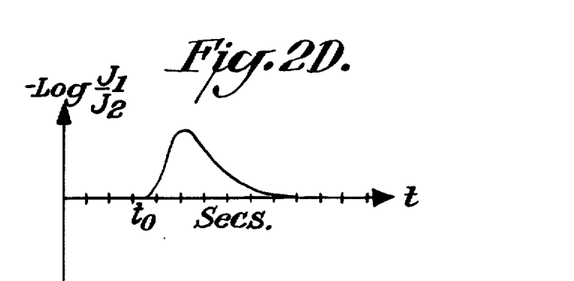
FIG. 2D is the waveform of FIG. 2C appearing at the output of the low pass filter and base line corrector circuit of FIG. 1.

A conventional low pass filter and base line corrector 31 is utilized to restore the waveform of FIG. 2C to its zero volt base line value, thereby effectively setting C = 0 in the final equation hereinbefore set forth expressing log $(J_1/J_2)$, and also limits the introduction of high frequency noise in the succeeding circuit. The resulting waveform is depicted in FIG. 2D, corresponding to that existing at point D, FIG. 1.

Figure 2E:
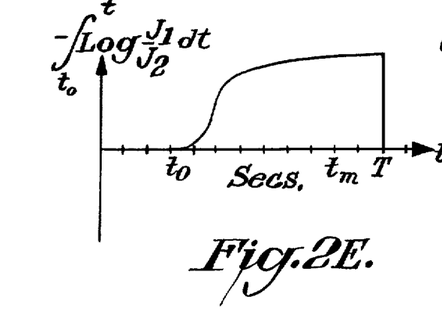
FIG. 2E is the waveform resulting from the input of FIG. 2D appearing at the integrator circuit output of FIG. 1.

The signal next passes to conventional integrator circuit 32, which effects the integration depicted in FIG. 2E corresponding to point E, FIG. 1. Conventional buffer 33 is employed to limit the output amplitudes of integrator 32 so that these will lie within the operating limits of the succeeding circuitry hereinafter described.

The preferred embodiment of apparatus shown in FIG. 1 employs sequential programming to obtain a high time rate of repetitive analyses automatically, it being understood that manual control can be substituted, if desired, however, under the penalty of obvious performance capability limitations.

A typical self-sequencing programmer, not detailed in the drawings, can be that marketed under the trade name AGASTAT by Amerace-Esna Corp., Elizabeth, N.J., which produces, in timed sequence, the electrical signals required to operate the system solenoid-actuated switches and electro-pneumatic valves (also not shown), which can typically be designs available from Skinner Precision Industries, Inc., New Britain, Conn.

Referring to FIG. 1, my preferred apparatus is designed to perform two different analyses at preselected times, the first being the usual routine monitoring of the effluent waste stream (denoted M in the drawing), which takes up the major operating time, and the second being occasional standardizations (denoted S) whenever these are deemed necessary.

Since the purpose of the waste stream monitoring is to obtain the concentration of trace material in the analyte (in p.p.m. or p.p.b.), the apparatus must be calibrated against standard solutions approximating concentrations of both the trace element and the same matrix background as will be encountered at the manufacturing plant site. Then the following equation applies:

$$\frac{m_M}{V} = \frac{m_S}{S}$$

where V is the volume concentration to be determined, S is the known standard solution volume concentration, and $m_M$ and $m_S$ are the monitored sample and standard sample trace element mass concentrations, respectively, which are measured as the output signals existing at point E during sample monitoring and standard analysis operation, respectively. From this, the monitored sample volume concentration V is readily determined, since $$V = S \frac{m_M}{m_S}$$

Since the term S of the foregoing equation is a known constant, its multiplying effect on the quotient of $m_M/m_S$ can be introduced by appropriate setting of the scale factor adjustment of recorder 43 hereinafter described.

Standard solutions are relatively stable over lengthy time periods and, thus, do not require frequent analytical confirmation if the value of $m_S$ is constantly available. This invention incorporates $m_S$ signal storage facilities in the form of the standard signal circuit switched into operation via taps S contacted by the ganged single-pole, double-throw switches 34 and 40.

Thus, the standardization term $m_S$ is determined by periodic analysis of samples of standard solution drawn from storage 16, thereby producing a characteristic $m_S$ signal by the same operation as hereinbefore described for effluent monitoring. With switches 34 and 40 closed on their S contacts, the $m_S$ signal is introduced into and stored in A/D converter 36, from which it is available at all times for read out by D/A converter 37 and application as the divisor term, via line 38, to conventional electrical signal M/S divider 35. The signal display equipment terminating in recorder 43 provides a representation of the concentration of the standard solution for the guidance of the operating staff.

Conversely, when switches 34 and 40 are closed on their M contacts, which is the usual switch position, successive readings of $m_M$ are supplied as the dividend term to divider 35, where division is performed and the resulting quotient signals passed to the display equipment in following circuit.

The apparatus display section comprises digital meter 41, which incorporates an integral A/D converter to convert the analog quotient signal received from M/S divider 35 into a digital reading and to provide storage for the measured signal. This is followed by a D/A converter 42 which restores the quotient signal to analog form, after which it passes to recorder 43 for quantitative display of the ppm (or ppb) volume concentration of the trace element monitored.

The operation of the apparatus of this invention is fully automatic, constituting, in sequence and under the time control of the cycling programmer hereinbefore described, injecting a metered sample followed by a metered amount of cleansing wash water into the open end of furnace 5, after which the radiation and electrical measurements are made during the relatively short interval (approximately 7 seconds) in which atomized sample exists in the line of radiation throughput.

Signal integration is completed by time $t_m$, shown on FIG. 2E, at which time the instantaneous amplitude value of the FIG. 2E waveform is transmitted to the divider circuit 35 for measurement or to the A/D converter circuit 36 for storage, as the position of switches 34 and 40 direct. At time T, FIG. 2E, the sequential programmer automatically returns the integrator 32 output to its zero volt base line value, thereby restoring the circuit to its original state for the next cycle of operation.

Figure 2F:
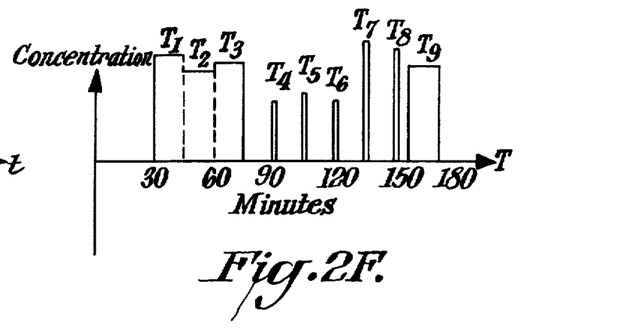
FIG. 2F is a typical recorder trace obtained over a prolonged monitoring period with the apparatus of FIG. 1.

FIG. 2F shows a typical recorder 43 trace over nine successive analysis cycles. Periods $T_1$-$T_3$ show the sequence of analyses conducted to establish a consistent $m_S$ value from standard solution 16 while the apparatus was operated in the calibration mode. In this mode, initiated by the operator's manual override of the programmer for each standard measurement, switches 34 and 40 and two-way valve 14 are all placed in S position, whereupon analyses of standard are conducted on the individual metered samples as each in turn is atomized and viewed during its short residence in furnace 5. As indicated by the large width traces of FIG. 2F, individual $m_S$ readouts can be maintained over unlimited time periods, because given $m_S$ values are stored in A/D converter 36 until superseded by the next-succeeding standardization.

When the operator is satisfied that the standard value, $m_S$, is valid, he switches the sequencing programmer to automatic control in the monitoring mode. Switches 34 and 40 are now turned to their M contacts, and two-way valve 14 is simultaneously turned to M position, thereby cutting off the supply circuit for standard solution 16 and substituting therefor sample supply to be monitored derived from macro sampler 15. The first trace element volume concentration measurement after calibration is, thus, $T_4$. This measurement is now based on the standard concentration value stored in the standardization analog-digital circuitry during the most recent standardization, $T_3$. Traces obtained through $T_8$ at preselected successive time intervals spaced about 15 minutes apart were recorded during automatic continuation of monitoring operation. Since traces $T_7$ and $T_8$ appear larger than normal, the operator initiated recalibration, as shown at $T_9$. It is seen that the amplitude of $T_9$ is close to that of $T_3$, verifying, by inference, that the apparatus is performing valid analyses and that $T_7$ and $T_8$ are indeed correct.

FIG. 3 shows the effectiveness of the apparatus of this invention in reducing a composite signal containing the absorption information of the trace element to an accurate usable form. In this instance the specimen monitored was a 5 percent aqueous solution of NaCl containing one ppm of Pb. The two high peak signal traces $a$ and $b$ represent, respectively, the absorbance (logarithmic) signals from the reference ($\sigma$) and analytical ($\pi$) radiations. These individual signal traces, constituting log $J_2$ and log $J_1$, respectively, were obtained via temporary connections made internally of log ratio circuit 30, and each show their relatively small Pb absorption portions in combination with the stronger background NaCl absorption. A 0.2 absorbance unit (A) magnitude scale is provided for reference.

Signals $c$ and $d$ are two successive log-ratioed intensities obtained by differencing the analytical ($\pi$) and the reference ($\sigma$) absorbance signals, and represent essentially the Pb mass alone.

Figure 4:
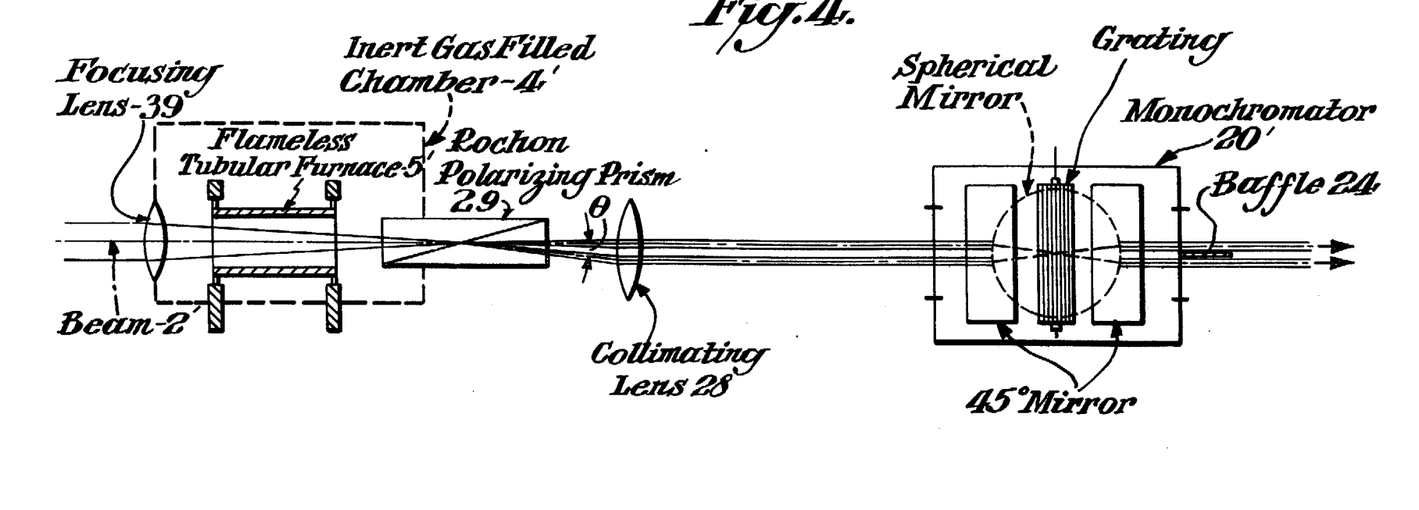
FIG. 4 is a schematic representation of an optical system which can be substituted for that of FIG. 1 for trace metal determinations in the ultra-violet spectral range.

Referring to FIG. 4, there is shown an embodiment of optical system which can be substituted for that of FIG. 1 for trace metal determinations having characteristic lines in the ultra-violet spectral range.

This design utilizes a Rochon polarizing prism 29 consisting of a $MgF_2$ crystal for spatially separating the incident beam 2' into its linear orthogonal polarization components. $MgF_2$ is particularly suited for broad band radiation use, since it can pass wavelengths which range from 1400 to 70,000A. However, the spatial separation of the two beams, which exit the same face of the crystal, becomes worse with increasing wavelength. Consequently, the $MgF_2$ crystal is most effective when analyzing materials which have characteristic wavelengths in the ultra-violet region. Experimentation shows that in the range 1400 to 2500A the angle of separation, $\theta$, between the two orthogonally polarized beams is between 4.5° to 5.5°. At 2500A the Glan-Taylor prism is no longer opaque and provides much better spatial separation of the two beams than the Rochon prism.

With the described capabilities of the $MgF_2$ Rochon prism, it is now possible to extend Zeeman effect atomic absorption analysis to arsenic, selenium, zinc and certain characteristic lines or mercury, which is beyond the capabilities of the Glan-Taylor polarizing prism arrangement.

Referring to FIG. 4, it will be understood that the showing here is limited to the changed optical apparatus only, all other components of the analyzer remaining the same as that already taught with reference to FIG. 1.

The radiation input to chamber 4' is first passed through a focusing lens 39 fitted to the inlet port of the inert gas-filled chamber in order to focus beam 2' on to the center of Rochon prism 29 after its passage through flameless tubular furnace 5'. Rochon prism 29 is disposed partly within chamber 4', i.e., towards lens 39, in order to reduce the focal distance of lens 39 so as to obtain a smaller image at the focus and, also, to maximize the prism-monochromator distance to allow ample room for adjustment of the collimating lens 28, which is disposed in optical line between chamber 4' and monochromator 20'. Collimating lens 28 maintains constant the spatial separation between the two beam components at the entrance port of monochromator 20'.

The apparatus of FIG. 4, using a $MgF_2$ Rochon prism polarizer and Zeeman effect atomic absorption, was utilized for the analysis of 5 $\mu$ liter samples containing 10 and 20 ppb concentrations of zinc in 0.5 percent aqueous NaCl solution. The Zn characteristic radiation of 2139A was employed as the analytical radiation and yielded a 0.36 absorbance signal for a 10 ppb Zn-containing sample.

It was determined that Zeeman effect analysis according to this invention consistently cancelled the salt absorbance to less than 0.03 absorbance unit, which is the equivalent of 0.8 ppb Zn, or one part in $5 \times 10^6$ of the mass of the NaCl present.

Although hollow cathode lamps of the type hereinbefore described with reference to radiation source 1 are preferred, electrodeless discharge lamps, such as those marketed by Ophthos Instrument Company and Perkin-Elmer Corporation can be substituted if desired.

What is claimed is:

1. Apparatus for acyclic spectrochemical trace analysis employing the Zeeman effect comprising, in optical train in the order recited, a radiation emission source emitting the characteristic spectral line radiation of an element to be analyzed, magnetic means applying a D-C magnetic field transverse the path of said characteristic radiation in the region of its emission maintaining a substantially steady D-C magnetic flux resolving said characteristic radiation into continuous linear orthogonally polarized radiation components a preselected one of which, the analytical beam, has a specific frequency characteristic of said element to be analyzed and a preselected other of which, the reference beam, has frequencies different from said analytical beam, furnace means open to the passage of said analytical beam and said reference beam for atomizing a sample of a substance to be analyzed, optical means segregating said analytical beam and said reference beam along separate courses according to their simultaneous linear orthogonal polarization directions and within preselected wavelength limits, each course being provided with electronic transducing means developing an electrical signal corresponding to the sensed radiation intensity of the respective beam viewed, means deriving the logarithmic ratio of said electrical signals one to the other, and means utilizing said logarithmic ratio in values specific to separate sample and standard analyses to give the concentration of said element to be analyzed in said sample.

2. Apparatus for acyclic spectrochemical trace analysis employing the Zeeman effect according to claim 1 wherein said radiation source comprises a hollow cathode lamp.

3. Apparatus for acylic spectrochemical trace analysis employing the Zeeman effect according to claim 1 wherein said magnetic means comprises a D-C magnet furnishing a noise-free constant D-C field in the range of about 2–15K gauss.

4. Apparatus for acyclic spectrochemical trace analysis employing the Zeeman effect according to claim 1 wherein said furnace means comprises an open cylinder fabricated from an electrically resistive metal having a length-to-diameter ratio of approximately 4.4 and a wall thickness preselected to afford a high enough electrical resistance to the passage of an electric current through said furnace means to obtain rapid heating of said furnace to the temperature of atomization of samples subjected to analysis.

5. Apparatus for acyclic spectrochemical trace analysis employing the Zeeman effect according to claim 1 wherein said optical means comprise a polarizing prism spatially separating said analytical beam and said reference beam and directing the beams to a monochromator producing strong narrow analytic and reference spectral lines.

6. Apparatus for acyclic spectrochemical trace analysis employing the Zeeman effect according to claim 1 provided with means for the introduction of discrete sample volumes into said furnace means.

7. Apparatus for acyclic spectrochemical trace analysis employing the Zeeman effect according to claim 1 wherein said means utilizing said logarithmic ratio values specific to separate sample and standard analyses to give the concentration of said element to be analyzed in said sample comprises means integrating said logarithmic ratio values over preselected time periods within which analysis is conducted.

8. Apparatus for acyclic spectrochemical trace analysis employing the Zeeman effect according to claim 7 wherein said means utilizing said logarithmic ratio to give the concentration of said element to be analyzed in said sample comprises means for obtaining and storing the integrated logarithmic ratio of sensed radiation intensities in said analytical and reference beams for a standard solution and means utilizing said standard solution integrated logarithmic ratio as a divisor of the integrated logarithmic ratio of sensed radiation intensities in said analytical and reference beams for a sample in analysis.

* * * * *

UNITED STATES PATENT OFFICE
CERTIFICATE OF CORRECTION

PATENT NO. : 3,937,577
DATED : FEBRUARY 10, 1976
INVENTOR(S) : ROBERT R. DORSCH

It is certified that error appears in the above-identified patent and that said Letters Patent are hereby corrected as shown below:

Col. 3, line 20, "2AA" should read --2A--.
Col. 4, line 21, "Lands" should read --Landé--.
Col. 4, line 32, "to" should read --of--.
Col. 7, line 3, "($\sigma$)" should read --($\pi$)--.
Col. 7, line 28, "c" should read --e--.
Col. 11, line 50, "or" should read --of--.

Signed and Sealed this twenty-seventh Day of April 1976

[SEAL]

Attest:

RUTH C. MASON
Attesting Officer

C. MARSHALL DANN
Commissioner of Patents and Trademarks